United States Patent [19]

Bailey

[11] Patent Number: 4,610,991
[45] Date of Patent: Sep. 9, 1986

[54] ANTIHYPERTENSIVE PYRIDYLAMINOBENZAMIDE COMPOUNDS

[75] Inventor: Denis M. Bailey, East Greenbush, N.Y.

[73] Assignee: Sterling Drug Inc., New York, N.Y.

[21] Appl. No.: 680,699

[22] Filed: Dec. 12, 1984

Related U.S. Application Data

[63] Continuation-in-part of Ser. No. 485,923, Apr. 18, 1983, abandoned, which is a continuation-in-part of Ser. No. 388,080, Jun. 14, 1982, abandoned.

[51] Int. Cl.⁴ .................. A61K 31/445; C07D 401/12
[52] U.S. Cl. ..................................... 514/318; 540/481; 540/597; 514/212; 514/229; 514/234; 514/252; 514/336; 514/340; 514/343; 514/352; 544/131; 544/360; 546/194; 546/281; 546/283; 546/284; 546/311; 546/312
[58] Field of Search ............... 546/194, 283, 284, 281, 546/311, 312; 544/131, 360; 260/244.4; 514/212, 318, 343, 336, 340, 352, 252, 229, 234

[56] References Cited

U.S. PATENT DOCUMENTS

| | | | |
|---|---|---|---|
| 3,174,972 | 3/1965 | Allais et al. | 546/161 |
| 3,226,394 | 12/1965 | Schipper | 546/337 |
| 3,632,761 | 1/1972 | Graham et al. | 546/161 |
| 3,875,165 | 4/1975 | Archibald et al. | 546/161 |
| 4,241,068 | 12/1980 | Schromm et al. | 546/161 X |

OTHER PUBLICATIONS

*The Pharmacologist*, vol. 25, No. 3, p. 101 (1983).
Ferrier, B., et al., *Chemistry & Industry*, 1089–1090 (1958).
Juby, P., et al., *J. Med. Chem.* 11, 111–117 (1968).
M. E. Konshin et al., (Perm. Gos. Farm. Inst., Perm, USSR) Deposited Document 1981, VINITI 2966-81 (Jun. 1, 1981) and sworn English translation.

*Primary Examiner*—Richard A. Schwartz
*Attorney, Agent, or Firm*—Thomas L. Johnson; B. Woodrow Wyatt; Paul E. Dupont

[57] ABSTRACT

A series of 4-pyridinylaminobenzamides, useful as antihypertensive agents, was prepared from the corresponding 4-pyridinylaminobenzoic acids by reacting the acid chloride of the latter with ammonia or a primary or secondary amine. Alternatively the compounds were prepared by reacting an aminobenzamide with 4-chloropyridine or equivalent reagent.

24 Claims, No Drawings

ANTIHYPERTENSIVE PYRIDYLAMINOBENZAMIDE COMPOUNDS

This application is a continuation-in-part of application Ser. No. 485,923, filed Apr. 18, 1983, now abandoned, which is in turn a continuation-in-part of application Ser. No. 388,080, filed June 14, 1982, now abandoned.

BACKGROUND OF THE INVENTION (1) Field of the Invention

The present invention relates to novel pyridylaminobenzamide compounds, their use as antihypertensive agents, and a method for their preparation.

(2) Information Disclosure Statement 2-(4-Pyridinylamino)benzoic acid [Ferrier and Campbell, *Chemistry & Industry* 1089 (1958)], an intermediate for the compounds of the instant invention, is inactive as an antihypertensive agent.

2-(Phenylamino)benzamide [Juby et al., *J. Med. Chem.* 11, 111 (1968)], a phenyl analog of the compounds of the instant invention, is inactive as an antihypertensive agent.

E. S. Schipper (Shulton Inc.) U.S. Pat. No. 3,226,394, issued Dec. 28, 1965 discloses a series of pyridylethylaminobenzamides having central nervous system depressant activity. Individual compounds disclosed include $2\beta$-(4-pyridyl)ethylaminobenzamide (Example 2) and $2\beta$-(4-pyridyl)ethylamino-N-(n-propyl)benzamide (Example 6).

B. E. Graham and W. Veldkamp (Upjohn) U.S. Pat. No. 3,632,761, issued Jan. 4, 1972 discloses a series of 4-quinolinylaminobenzamides having antihypertensive and anti-anxiety activity. Preparation 3 describes the preparation of 1-[4-(7-chloro-4-quinolinylamino)benzoyl]piperidine.

M. E. Konshin and N. P. Khokhryakova (Perm. Gos. Farm. Inst., Perm, USSR) Deposited Document 1981 VINITI 2966-81 (June 1, 1981) describe the synthesis and antimicrobial activity of arylamides of N-(4-pyridyl)anthranilic acid.

Information on the pharmacological properties of the preferred species of the present invention has been published in *The Pharmacologist*, Vol. 25, No. 3, p. 101 (1983) under the following titles: Antihypertensive Activity of Win 48049 (1-[2-(4-pyridinylamino)benzoyl]piperidine) in the Hypertensive Rat, Dog and Monkey, by Harlan Lape, Albert DeFelice and Denis Bailey; and Direct Vasodilator and Sympatholytic Activities of Win 48049, a New Antihypertensive, in Experimental Animals, by A. DeFelice and H. Lape (Sterling-Winthrop Research Institute, Rensselaer, N.Y.).

SUMMARY OF THE INVENTION

In a product aspect, the invention relates to compounds having the formula

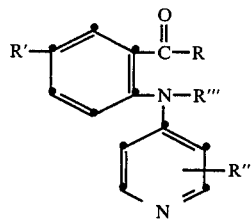

wherein R is $NH_2$, NH-alkyl having 1–7 carbon atoms, 2-furanylmethylamino, 2-thienylmethylamino, N(alkyl)$_2$ having 2–5 carbon atoms, 1-morpholinyl, 4-methyl-1-piperazinyl, or

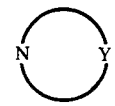

wherein

Y is a straight or branched chain alkylene radical having 4–8 carbon atoms and forming with the nitrogen atom a 5–8 membered ring, optionally substituted by a hydroxy group;

R' is H, $O_2N$, halogen, alkyl of 1–3 carbon atoms, alkoxy of 1–3 carbon atoms, HO or $Z=NO_2S$, where $Z=N$ is amino, phenylamino, benzylamino, 4-methylbenzylamino, alkylamino or dialkylamino, alkyl having 1–3 carbon atoms;

R" is H or alkyl of 1–3 carbon atoms; and

R''' is H, 2-propenyl or alkyl of 1–3 carbon atoms; or a pharmaceutically acceptable acid-addition or quaternary ammonium salt thereof.

In a further product aspect, the invention relates to certain position isomers of compounds of Formula I where the pyridinylamino group is in the meta or para position with respect to the amide functional group.

In a still further product aspect, the invention relates to compositions for lowering the blood pressure of a hypertensive mammal which comprise an antihypertensively effective amount of a compound of Formula I together with one or more pharmaceutically acceptable excipients.

In a process aspect the invention relates to a process for preparing a compound of Formula I where R' is other than hydroxy which comprises converting a compound having the formula

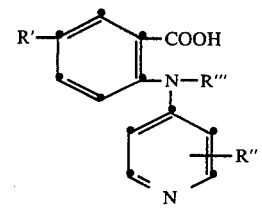

to its acid chloride and reacting the latter with a compound of the formula H-R.

In a further process aspect the invention relates to a process for preparing a compound of Formula I which comprises reacting a compound having the formula

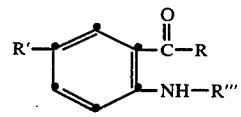

or an acid-addition salt thereof with 4-chloropyridine, an alkylated 4-chloropyridine, an acid-addition salt of said chloropyridine, or N-(4-pyridyl)pyridinium chloride hydrochloride.

In a still further process aspect, the invention relates to a method for lowering the blood pressure of a hypertensive mammal which comprises administering to said mammal a composition comprising an antihypertensively effective amount of a compound of Formula I.

DETAILED DESCRIPTION INCLUSIVE OF PREFERRED EMBODIMENTS

In the process involving the reaction of the acid chloride of compound of Formula II with ammonia or an amine (H-R), the reaction takes place readily in an inert solvent at ambient temperature. The acid chloride can be formed from the free acid (II) by treatment with reagents known to convert carboxylic acids to acid chlorides, e.g. phosphorus trichloride, phosphorus pentachloride, thionyl chloride or oxalyl chloride. Thionyl chloride is a preferred reagent.

The intermediates of Formula II are in turn prepared by reacting 2-aminobenzoic acid or a derivative thereof:

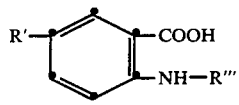

with 4-chloropyridine or an alkylated 4-chloropyridine or an acid-addition salt of said chloropyridines. The reaction takes place by heating the reactants in acetic acid medium at a temperature of about 100°–125° C., conveniently at the boiling temperature of the acetic acid. The intermediate of Formula II is obtained in the form of its hydrochloride salt. The latter can be readily converted to the free base with an alkaline substance such as sodium acetate. It is also possible to carry out the reaction between the aminobenzoic acid or derivative thereof with a 4-chloropyridine in an inert solvent at 100°–175° C. in the presence of a tertiary amine such as triethylamine.

In an alternative process the pyridinyl group is introduced as the last step by causing an intermediate of Formula III to react with 4-chloropyridine or an alkylated 4-chloropyridine, or an acid-addition salt thereof, according to the procedure described in the preceding paragraph. The intermediates of Formula III are in turn prepared by reaction of the appropriate amine H-R with isatoic anhydride or a derivative thereof of the formula

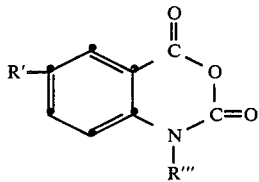

In place of 4-chloropyridine as a reagent for introducing the pyridinyl group it is possible to use N-(4-pyridinyl)pyridinium chloride hydrochloride in accordance with the general method described by Jerchel and Jakob, Chem. Ber. 91, 1266 (1959). The reaction takes place by heating a compound of Formula III, preferably in the form of an acid-addition salt, with N-(4-pyridinyl)pyridinium chloride hydrochloride either alone or in an inert solvent such as sulfolane, dimethylsulfoxide, phenol or cellosolve at a temperature between about 100° C. and 200° C.

The compounds of Formula I wherein R' is hydroxy are preferably prepared by demethylation of the compounds wherein R' is methoxy. A preferred demethylation procedure comprises treating the methoxy compound with boron tribromide.

The compounds of Formula I wherein R' is bromo or nitro are prepared by conventional bromination or nitration, respectively, of the corresponding compounds of Formula I wherein R' is hydrogen. Alternatively, the bromination or nitration can be carried out, if desired, at an intermediate stage of the synthesis, for example, on a compound of Formula II or III or precursor thereof where R' is hydrogen.

The compounds of Formula I where R' is Z=NO$_2$S are preferably prepared by reacting a compound of Formula I where R' is hydrogen first with chlorosulfuric acid and then with ammonia or an amine, Z=NH. Alternatively, the aminosulfonyl group can be introduced at an intermediate stage, e.g., in a compound of Formula III where R' is hydrogen.

If compounds of Formula I where R''' is alkyl or 2-propenyl are desired, the R''' substituent can be introduced into a compound of Formula I, II or III where R''' is hydrogen by reaction with an alkyl halide or 2-propenyl halide in the presence of a strong base such as sodium hydride.

The invention also contemplates pharmaceutically acceptable acid-addition salts of the compounds of Formula I. The nature of the acid-addition salt is immaterial provided it is derived from an acid the anion of which is essentially innocuous to animal organisms. Examples of appropriate acid-addition salts include the hydrochloride, hydrobromide, sulfate, methanesulfonate, maleate, citrate, tartrate, p-toluenesulfonate, cyclohexanesulfamate, and the like. Although the compounds of Formula I theoretically possess two basic nitrogen atoms, the compounds tend to form only stable monoacid-addition salts.

Also contemplated are pharmaceutically acceptable quaternary ammonium salts of the compounds of Formula I, including those derived from lower-alkyl halides, alkanesulfonates or arylsulfonates.

EXAMPLE 1

(a) 2-(4-Pyridinylamino)benzoic acid [II; R', R'', R''' are H].

A suspension of 274.5 g (2.0 moles) of anthranilic acid, 300 g (2.0 moles) of 4-chloropyridine hydrochloride and 180 g (2.19 moles) of anhydrous sodium acetate in 855 ml of glacial acetic acid was stirred at reflux for three hours. The mixture was cooled to room temperature and the precipitated solid was filtered. The product was washed with a small amount of cold acetic acid followed by cold ether. It was dried at 75° C., in vacuo to give 428 g (85.6%) of 2-(4-pyridinylamino)benzoic acid as the hydrochloride salt, m.p. 275°–280° C.(decompn.).

The salt was dissolved in 1500 ml of boiling water and a solution of 155 g (1.89 moles) of anhydrous sodium acetate in 350 ml of water was added. The mixture was cooled in ice-water and the product was filtered and washed with cold water. After drying, 244 g (57%) of 2-(4-pyridinylamino)benzoic acid was obtained, m.p. 282°–286° C.

(b) 1-[2-(4-Pyridinylamino)benzoyl]piperidine [I; R is 1-piperidinyl; R', R'', R''' are H].

2-(4-Pyridinylamino)benzoic acid (244 g, 1.14 moles) was added with stirring at room temperature to 1.4 liters of thionyl chloride containing a catalytic amount (about 1.4 ml) of N,N-dimethylformamide. A mildly exothermic reaction ensued. The reaction was stirred at room temperature for 3 hours when the excess thionyl chloride was removed in vacuo. The residual oil was azeotroped twice with toluene. The yellowish gummy acid chloride was suspended in 1.5 liters of acetonitrile and 556 ml of piperidine was added with cooling (15°–20° C.) and stirring. Stirring was continued for 3 hours. The precipitated white solid was filtered and washed with a little cold acetonitrile. It was slurried once in about 2 liters of water while adjusting the pH to 9 by addition of potassium carbonate. The solid was dried and recrystallized from 2.7 liters of ethyl acetate to afford 166 g (51.6%) of 1-[2-(4-pyridinylamino)benzoyl]piperidine, m.p. 153°–156° C.

The methiodide quanternary salt of 1-[2-(4-pyridinylamino)benzoyl]piperidine, m.p. 178°–180° C., was prepared by reacting the free base with a molar equivalent amount of methyl iodide in acetonitrile.

EXAMPLE 2

(a) 1-(2-Aminobenzoyl)piperidine.

Piperidine (1.63 liter) was added over a period of 30 minutes to a slurry of 2.5 kg isatoic anhydride in 12.5 liters of toluene. The reaction mixture was stirred for 20 minutes and extracted four times with 5 liters of 1.2N hydrochloric acid. The extracts were made basic and the product extracted with 12.5 liters of isopropyl acetate. The organic layer was washed with water and saturated sodium chloride solution and then concentrated to a thick slurry with a volume of 4 liters. The solid product was collected, washed with cold isopropyl acetate and dried overnight in vacuo to give 2.22 kg of 1-(2-aminobenzoyl)piperidine. Concentration of the filtrate afforded a second crop of 0.23 kg.

(b) 1-[2-(4-Pyridinylamino)benzoyl]piperidine [I; R is 1-piperidinyl; R', R", R'" are H].

A solution of 2.77 kg 1-(2-aminobenzoyl)piperidine in 16 liters of 2-methoxyethanol was heated until solvent distillation was about to begin (125° C. internal temperature). A solution of 2.1 kg 4-chloropyridine hydrochloride in 21 liters of 2-methoxyethanol was then slowly added over a period of one hour during which 4 liters of distillate was collected. Heating was continued for another hour while 16 liters of distillate was collected. The reaction mixture was concentrated in vacuo, and the thick residue was dissolved in 10 liters of water. Sodium acetate trihydrate (1.85 kg) was added and the solution washed three times with 3 liters of isopropyl acetate and decolorized with activated charcoal. The aqueous solution was made basic (pH>10) by dropwise addition of sodium hydroxide solution. Seeding during the addition generated a precipitate. A small amount of acetic acid was added to lower the pH to 8.5–9, and after 30 minutes of stirring the product was collected, washed with water and air dried to give 2.51 kg of 1-[2-(4-pyridinylamino)benzoyl]piperidine, m.p. 152°–153° C. The latter product was further purified by recrystallization from acetone to give the compound with m.p. 154°–155° C.

The compounds of the following Examples 3–28 were prepared in accordance with the procedure described in Example 1, part (b), using the appropriate amine reactant (H-R).

EXAMPLE 3

N-Methyl-2-(4-pyridinylamino)benzamide [I; R is NH(CH$_3$); R', R", R'" are H], m.p. 174°–176° C., colorless powder from absolute ethanol (60% yield).

EXAMPLE 4

N,N-Dimethyl-2-(4-pyridinylamino)benzamide [I; R is N(CH$_3$)$_2$; R', R", R'" are H], m.p. 167°–168° C., colorless powder from ethanol (84% yield).

EXAMPLE 5

1-[2-(4-Pyridinylamino)benzoyl]pyrrolidine [I; R is 1-pyrrolidinyl; R', R", R'" are H], m.p. 161°–163° C., colorless powder from ethyl acetate (55% yield).

EXAMPLE 6

N-Ethyl-2-(4-pyridinylamino)benzamide [I; R is NHC$_2$H$_5$; R', R", R'" are H], m.p. 166°–167° C., colorless powder from ethanol (53% yield).

EXAMPLE 7

N-(n-Butyl)-2-(4-pyridinylamino)benzamide [I; R is NH(CH$_2$)$_3$CH$_3$; R', R", R'" are H], m.p. 122°–124° C., tan powder from ethyl acetate (46% yield).

EXAMPLE 8

N-(t-Butyl)-2-(4-pyridinylethyl)benzamide [I; R is NHC(CH$_3$)$_3$; R', R", R'" are H], m.p. 195°–197° C., colorless crystals from dimethylformamide (49% yield).

EXAMPLE 9

N-Isopropyl-2-(4-pyridinylamino)benzamide [I; R is NHCH(CH$_3$)$_2$; R', R", R'" are H], m.p. 189°–191° C., colorless powder from methanol (64% yield).

EXAMPLE 10

N-(n-Hexyl)-2-(4-pyridinylamino)benzamide [I; R is NH(CH$_2$)$_5$CH$_3$; R', R", R'" are H], m.p. 99°–101° C., tan powder from ethyl acetate—hexane (77% yield).

EXAMPLE 11

N-(n-Propyl)-2-(4-pyridinylamino)benzamide [I; R is NH(CH$_2$)$_2$CH$_3$; R', R", R'" are H], m.p. 136°–138° C., colorless powder from ethyl acetate (68% yield).

EXAMPLE 12

N-(n-Pentyl)-2-(4-pyridinylamino)benzamide [I; R is NH(CH$_2$)$_4$CH$_3$; R', R", R'" are H], m.p. 90°–92° C., colorless powder from ether (63.5% yield).

EXAMPLE 13

N,N-Diethyl-2-(4-pyridinylamino)benzamide [I; R is N(C$_2$H$_5$)$_2$; R', R", R'" are H], m.p. 146°–148° C., tan powder from isopropyl acetate (58% yield).

EXAMPLE 14

Hexahydro-1-[2-(4-pyridinylamino)benzoyl]azepine [I; R is hexamethylenimino; R', R", R'" are H], hydrochloride salt, m.p. 236°–238° C., colorless powder from ethanol (27% yield).

EXAMPLE 15

Octahydro-1-[2-(4-pyridinylamino)benzoyl]azocine [I; R is heptamethylenimino; R', R", R'" are H], m.p. 164°–166° C., tan powder from acetone—methanol (73% yield).

EXAMPLE 16

N-Ethyl-N-methyl-2-(4-pyridinylamino)benzamide [I; R is N(CH$_3$)(C$_2$H$_5$); R', R", R'" are H], m.p. 103°–105° C., colorless powder from ether (38% yield).

EXAMPLE 17

N-(n-Heptyl)-2-(4-pyridinylamino)benzamide [I; R is NH(CH$_2$)$_6$CH$_3$; R', R", R''' are H], m.p. 96°–98° C., colorless crystals from ether (22% yield).

EXAMPLE 18

N-Ethyl-N-(n-propyl)-2-(4-pyridinylamino)benzamide [I; R is N(CH$_3$)(CH$_2$CH$_2$CH$_3$); R', R", R''' are H], yellow solid, converted with methanolic hydrogen chloride to the hydrochloride salt, m.p. 133°–135° C. (45% yield).

EXAMPLE 19

4-Methyl-1-[2-(4-pyridinylamino)benzoyl]piperidine [I; R is 4-methyl-1-piperidinyl; R', R", R''' are H], m.p. 118.5°–120° C., buff powder from ethyl acetate—ether (27% yield).

EXAMPLE 20

3-Methyl-1-[2-(4-pyridinylamino)benzoyl]piperidine [I; R is 3-methyl-1-piperidinyl; R', R", R''' are H], m.p. 135°–137° C., colorless powder from acetone (38% yield).

EXAMPLE 21

2-Methyl-1-[2-pyridinylamino)benzoyl]piperidine [I; R is 2-methyl-1-piperidinyl; R', R", R''' are H], m.p. 157°–159° C., colorless powder from ethyl acetate (56.6% yield).

EXAMPLE 22

2-Ethyl-1-[2-(4-pyridinylamino)benzoyl]piperidine [I; R is 2-ethyl-1-piperidinyl; R', R", R''' are H], m.p. 142°–143° C., colorless powder from acetone (41% yield).

EXAMPLE 23

4-[2-(4-Pyridinylamino)benzoyl]morpholine [I; R is 1-morpholinyl; R', R", R''' are H], m.p. 168°–170° C., colorless powder from ethanol—ether (61% yield).

EXAMPLE 24

4-Methyl-1-[2-(4-pyridinylamino)benzoyl]piperazine [I; R is 4-methyl-1-piperazinyl; R', R", R''' are H], m.p. 135°–137° C., colorless powder from ethyl acetate (72% yield).

EXAMPLE 25

N-(2-Furanylmethyl)-2-(4-pyridinylamino)benzamide [I; R is 2-furanylmethylamino; R', R", R''' are H], m.p. 141°–142.5° C., colorless powder from ethyl acetate—ether (68% yield).

EXAMPLE 26

2-(4-Pyridinylamino)-N-(2-thienylmethyl)benzamide [I; R is 2-thienylmethylamino; R', R", R''' are H], m.p. 135°–136° C., colorless powder from acetonitrile (33% yield).

EXAMPLE 27

1-[2-(4-Pyridinylamino)benzoyl]-4-piperidinol [I: R is 4-hydroxy-1-piperidinyl; R', R", R''' are H], m.p. 145°–147° C., colorless powder from acetonitrile (42% yield).

EXAMPLE 28

1-[2-(4-Pyridinylamino)benzoyl]-3-piperidinol [I; R is 3-hydroxy-1-piperidinyl; R', R", R''' are H], m.p. 198°–199° C., colorless powder from acetone (25% yield).

EXAMPLE 29

(a) 5-Chloro-2-(4-pyridinylamino)benzoic acid was prepared from 25 g of 5-chloroanthranilic acid and 21 g of 4-chloropyridine hydrochloride according to the procedure of Example 1, part (a). There was obtained 14.2 g of 5-chloro-2-(4-pyridinylamino)benzoic acid, m.p. 306°–308° C. (decompn.).

(b) 1-[5-Chloro-2-(4-pyridinylamino)benzoyl]piperidine [I; R is 1-piperidinyl; R' is Cl; R", R''' are H] was prepared by converting 12.4 g of 5-chloro-2-(4-pyridinylamino)benzoic acid to its acid chloride and reacting the latter with piperidine according to the procedure of Example 1, part (b). There was obtained 10.16 g of 1-[5-chloro-2-(4-pyridinylamino)benzoyl]piperidine as a colorless powder, m.p. 158°–159° C., when recrystallized from acetone.

EXAMPLE 30

(a) 5-Methoxy-2-(4-pyridinylamino)benzoic acid was prepared from 4.9 g of 5-methoxyanthranilic acid and 4.4 g of 4-chloropyridine hydrochloride according to the procedure of Example 1, part (a). There was obtained 8.0 g of 5-methoxy-2-(4-pyridinylamino)benzoic acid which was recrystallized from water and used directly in the next reaction.

(b) 1-[5-Methoxy-2-(4-pyridinylamino)benzoyl]piperidine [I; R is 1-piperidinyl; R' is CH$_3$O; R", R''' are H] was prepared by converting 8.1 g of 5-methoxy-2-(4-pyridinylamino)benzoic acid to its acid chloride and reacting the latter with piperidine according to the procedure of Example 1, part (b). There was obtained 5.4 g of 1-[5-methoxy-2-(4-pyridinylamino)benzoyl]piperidine, m.p. 176°–178° C. when recrystallized from ethyl acetate. A further recrystallization from acetonitrile gave a sample with the m.p. 187°–188° C.

EXAMPLE 31

1-[5-Hydroxy-2-(4-pyridinylamino)benzoyl]piperidine [I; R is 1-piperidinyl; R' is HO; R", R''' are H].

1-[5-Methoxy-2-(4-pyridinylamino)benzoyl]piperidine (Example 30b) (9.2 g) was dissolved in 100 ml of methylene dichloride. To this solution was added dropwise 80 ml of boron tribromide solution (0.8M in methylene dichloride). The mixture was kept at room temperature overnight and the solvent removed at reduced pressure. The residue was made basic with aqueous potassium carbonate and the solid product collected by filtration. The product was dissolved in methanol and acetonitrile added to produce 4.9 g of 1-[5-hydroxy-2-(4-pyridinylamino)benzoyl]piperidine. A further recrystallization from methanol gave a sample with m.p. 242°–243° C.(decompn.).

EXAMPLE 32

1-[5-Nitro-2-(4-pyridinylamino)benzoyl]piperidine [I; R is 1-piperidinyl; R' is O$_2$N; R", R''' are H].

To a solution of 20 g of 1-[2-(4-pyridinylamino)benzoyl]piperidine (Example 1b) in 75 ml of sulfuric acid cooled in an ice-salt bath was slowly added a solution of 6.5 ml of concentrated nitric acid in 65 ml of sulfuric acid. The mixture was stirred at 5° C. for four hours and then poured onto ice and allowed to stand overnight. A crystalline acid-addition salt formed which was collected, dissolved in water and converted to the free base by adding sodium bicarbonate. The free base product was extracted with methylene dichloride, the extracts dried over anhydrous sodium sulfate and concentrated, and the residue triturated with ethyl acetate to give 9.3 g of 1-[5-nitro-2-(4-pyridinylamino)benzoyl]piperidine as a yellow powder, m.p. 194°–196° C.(decompn.).

EXAMPLE 33

2-(4-Pyridinylamino)benzamide [I; R is $NH_2$; R', R", R'" are H].

To a solution of 13.6 g (0.1 mole) of anthranilamide in 35 ml of glacial acetic acid was added in order 15 g (0.1 mole) of 4-chloropyridine hydrochloride and 9.0 g (0.11 mole) of anhydrous sodium acetate. The resulting suspension was heated at reflux for five hours. The reaction mixture was concentrated under reduced pressure to give a yellow solid which was dissolved in 250 ml of water and made basic with 2.5N sodium hydroxide solution. The solid which separated was collected, washed with water and dried to give 14 g of product. A portion of the latter was recrystallized from methanol to give the free base form of 2-(4-pyridinylamino)benzamide, m.p. 206°–209° C. A further portion of the crude free base was treated with methanolic hydrogen chloride to produce the hydrochloride salt form, m.p. 218°–220° C. when recrystallized from methanol—ether.

EXAMPLE 34

5-Bromo-2-(4-pyridinylamino)benzamide [I; R is $NH_2$; R' is Br; R", R'" are H].

To a solution of 25 g (0.12 mole) of 2-(4-pyridinylamino)benzamide (Example 33) in 125 ml of acetic acid at 12° C. was added dropwise 70 ml (0.12 mole) of bromine in acetic acid (0.002 molar). The reaction mixture was allowed to come to room temperature for three hours and then concentrated at reduced pressure to remove the acetic acid. The residue was made basic with 50% sodium hydroxide solution, and the resulting solid was dissolved in 500 ml of hot dimethylformamide and allowed to crystallize upon cooling to give 17.1 g of product. A further recrystallization from aqueous dimethylformamide gave 15 g of 5-bromo-2-(4-pyridinylamino)benzamide, pale yellow needles, m.p. 298°–299° C.(decompn.).

EXAMPLE 35

1-[5-Aminosulfonyl-2-(4-pyridinylamino)benzoyl]piperidine [I; R is 1-piperidinyl; R' is $H_2NO_2S$; R" and R'" are H].

A mixture of 10.0 g (0.0356 mole) of 1-[2-(4-pyridinylamino)benzoyl]piperidine (Example 1b) and 20 ml (0.3 mole) of chlorosulfonic acid was heated on a steam bath for 10 minutes and then poured onto 400 g of ice. When the ice had melted, the solid material was collected and suspended in 70 ml of acetonitrile. Concentrated ammonium hydroxide (80 ml) was then added and the mixture stirred at room temperature overnight. The reaction mixture was extracted with ethyl acetate and chloroform, and the extracts dried over anhydrous sodium sulfate and evaporated. The residue was recrystallized from an ethyl acetate—ether mixture to give 2.6 g of 1-[5-aminosulfonyl-2-(4-pyridinylamino)benzoyl]piperidine in the form of a monohydrate, m.p. 212°–214° C.

EXAMPLE 36

1-[5-(Dimethylaminosulfonyl)-2-(4-pyridinylamino)benzoyl]piperidine [I; R is 1-piperidinyl; R' is $(CH_3)_2NO_2S$, R" and R'" are H] was prepared by the procedure of Example 35 wherein the acetonitrile—ammonium hydroxide solution was replaced by a solution of acetonitrile saturated with dimethylamine. The product was obtained in 38% yield and had m.p. 214°–216° C. when recrystallized from ethyl acetate.

EXAMPLE 37

1-[5-(Methylaminosulfonyl)-2-(4-pyridinylamino)benzoyl]piperidine [I; R is 1-piperidinyl; R' is $CH_3NHSO_2$; R" and R'" are H] was prepared by the procedure of Example 35 wherein the acetonitrile—ammonium hydroxide solution was replaced by a solution of acetonitrile saturated with methylamine. The product was obtained in 37% yield and had m.p. 178°–180° C. when recrystallized from acetone.

EXAMPLE 38

1-[5-(Phenylaminosulfonyl)-2-(4-pyridinylamino)benzoyl]piperidine [I; R is 1-piperidinyl; R' is $C_6H_5NHSO_2$; R" and R'" are H] was prepared by the procedure of Example 35 wherein the acetonitrile—ammonium hydroxide solution was replaced by a solution of aniline in acetonitrile. The product was obtained in 16% yield and had m.p. 199°–200° C. when recrystallized from ethyl acetate.

EXAMPLE 39

1-[5-(Benzylaminosulfonyl)-2-(4-pyridinylamino)benzoyl]piperidine [I; R is 1-piperidinyl; R' is $C_6H_5CH_2NHSO_2$; R" and R'" are H] was prepared by the procedure of Example 35 wherein the acetonitrile—ammonium hydroxide solution was replaced by a solution of benzylamine in acetonitrile. The product was obtained in about 20% yield and had m.p. 183°–185° C. when recrystallized from an ethyl acetate—ether mixture.

EXAMPLE 40

1-[5-(Ethylaminosulfonyl)-2-(4-pyridinylamino)benzoyl]piperidine [I; R is 1-piperidinyl; R' is $C_2H_5NHSO_2$; R" and R'" are H] was prepared by the procedure of Example 35 wherein the acetonitrile—ammonium hydroxide solution was replaced by a solution of acetonitrile saturated with ethylamine. The product was obtained in about 40% yield and had m.p. 139°–142° C. when recrystallized from an ethyl acetate—ether mixture.

EXAMPLE 41

1-[5-(Methylaminosulfonyl)-2-(4-pyridinylamino)benzoyl]pyrrolidine [I; R is 1-pyrrolidinyl; R' is $CH_3NHSO_2$; R" and R'" are H] was prepared from 1-[2-(4-pyridinylamino)benzoyl]pyrrolidine (Example 5), chlorosulfonic acid, and a solution of methylamine in acetonitrile according to the procedure of Example 35. The product was obtained in 35% yield and had m.p. 158°–160° C. when recrystallized from an ethyl acetate—ether mixture.

EXAMPLE 42

1-[5-(4-Methylbenzylaminosulfonyl)-2-(4-pyridinylamino)benzoyl]piperidine [I; R is 1-piperidinyl; R' is 4-$CH_3$-$C_6H_4CH_2NHSO_2$; R" and R'" are H]

was prepared by the procedure of Example 35 wherein the acetonitrile—ammonium hydroxide solution was replaced by a solution of 4-methylbenzylamine in acetonitrile. The product was obtained in 23% yield and had m.p. 178°–180° C. when crystallized from a chloroform—ether mixture.

EXAMPLE 43

1-[2-(2-Methyl-4-pyridinylamino)benzoyl]piperidine [I; R is 1-piperidinyl; R' is H, R" is 2-CH$_3$, R''' is H].

A mixture of 18.2 g of 1-(2-aminobenzoyl)piperidine and 12.2 g of 2-methyl-4-chloropyridine in 5.0 ml of acetic acid was heated at reflux for six hours and then kept at room temperature overnight. The reaction mixture was concentrated in vacuo, and the residue treated with dilute acid to pH 2 and extracted with methylene dichloride. The aqueous layer was made basic with potassium carbonate and extracted with chloroform. Further work-up of this solution afforded 2.58 g of 1-[2-(2-methyl-4-pyridinylamino)benzoyl]piperidine, m.p. 93°–95° C. when recrystallized from ethyl acetate—ether—hexane.

EXAMPLE 44

(a) 1-(2-Methylaminobenzoyl)piperidine.

A mixture of 17.7 g (0.1 mole) of N-methylisatoic anhydride and 17.03 g (0.2 mole) of piperidine in 50 ml of dimethylformamide was stirred overnight at room temperature. The reaction mixture was concentrated in vacuo and the residue mixed with 50 ml potassium carbonate solution. The resulting brown solid was collected and dissolved in chloroform. The chloroform solution was washed with potassium carbonate, filtered, dried over anhydrous sodium sulfate and concentrated to give 18.1 g of colorless solid used directly in the following reaction.

(b) 1-{2-[Methyl-(4-pyridinyl)amino]benzoyl}piperidine [I; R is 1-piperidinyl; R', R" are H; R''' is CH$_3$].

A mixture of 17.4 g (0.08 mole) of 1-(2-methylaminobenzoyl)piperidine, 9.1 g (0.08 mole) of 4-chloropyridine, 5.8 ml of triethylamine and 40 ml of dimethylformamide was heated at reflux for 46 hours. The reaction mixture was concentrated in vacuo and the residue triturated with acetone. The suspension was filtered, the filtrate concentrated, and the residue made basic with aqueous potassium carbonate and extracted with chloroform. From the latter extracts there was obtained 2.1 g of solid which was recrystallized from ethyl acetate to afford 1-{2-[methyl-(4-pyridinyl)amino]benzoyl}piperidine, as a tan powder, m.p. 109.5°–111.0° C.

EXAMPLE 45

1-{2-[Ethyl-(4-pyridinyl)amino]benzoyl}piperidine [I; R is 1-piperidinyl; R', R" are H; R''' is C$_2$H$_5$].

A solution of 22.4 g of 1-[2-(4-pyridinylamino)benzoyl]piperidine (Example 1b) in 45 ml of dimethylformamide was added dropwise to a suspension of sodium amide (from 4.8 g of 50% oil suspension, washed free of oil) in 115 ml of dimethylformamide. The mixture was stirred for one hour, and then 6.5 g of ethyl iodide was added dropwise. The reaction mixture was stirred for two hours, then filtered and concentrated in vacuo. The residue was partitioned between water and ether and the ether-soluble material recovered (15.2 g). The latter was recrystallized from ethyl acetate—pentane to give 13 g of 1-{2-[ethyl-(4-pyridinyl)amino]benzoyl}piperidine, m.p. 123°–124° C.

EXAMPLE 46

1-{2-[2-Propenyl-(4-pyridinyl)amino]benzoyl}piperidine [I; R is 1-piperidinyl; R', R" are H; R''' is C$_3$H$_5$] was prepared according to the procedure of Example 45 while substituting allyl bromide for ethyl iodide, and was obtained in 64% yield in the form of a pale yellow powder, m.p. 87°–89° C., when recrystallized from ether.

EXAMPLE 47

1-{2-[Propyl-(4-pyridinyl)amino]benzoyl}piperidine [I; R is 1-piperidinyl; R' and R" are H; R''' is (CH$_2$)$_2$CH$_3$] was prepared according to the procedure of Example 45 while substituting n-propyl bromide for ethyl iodide, and was obtained in 34% yield in the form of a colorless solid, m.p. 40°–42° C.

EXAMPLE 48

(a) 4-(4-Pyridinylamino)benzoic acid was prepared from 76.6 g of 4-aminobenzoic acid and 63.5 g of 4-chloropyridine in 240 ml of acetic acid, heated at reflux for 6 hours. With a work-up procedure similar to that of Example 33, there was obtained 50 g of product with the m.p. 322°–324° C.(decompn.).

(b) 4-(4-Pyridinylamino)benzamide.

4-(4-Pyridinylamino)benzoic acid (43 g), 400 ml of thionyl chloride and 0.4 ml of dimethylformamide were mixed at 0° C. The mixture was heated on a steam bath for about 19 hours. The excess thionyl chloride was removed under reduced pressure and the residue azeotroped twice with toluene. The resulting acid chloride was suspended in 300 ml of acetonitrile. The suspension was cooled to 0° C. and an ice-cold solution of 0.8 ml of ammonia in 250 ml of acetonitrile was added dropwise over a period of 20 minutes. The reaction mixture was stirred for four hours and the solid material collected by filtration. The latter was slurried in 1 liter of water and 25 ml of saturated aqueous potassium carbonate was added. The solid product was collected and recrystallized twice from methanol to give 22 g of 4-(4-pyridinylamino)benzamide, m.p. 223°–226° C. A further recrystallization gave a sample with the m.p. 225.5°–227.5° C.

EXAMPLE 49

1-[4-(4-Pyridinylamino)benzoyl]piperidine was prepared from 4-(4-pyridinylamino)benzoic acid and piperidine according to a procedure analogous to that of Example 48(b), and was obtained in 49.5% yield in the form of a buff powder, m.p. 170°–172° C. when recrystallized from acetonitrile.

EXAMPLE 50

(a) 3-(4-Pyridinylamino)benzoic acid was prepared from 41.1 g of m-aminobenzoic acid and 34.0 g of 4-chloropyridine in 110 ml of acetic acid, heated at reflux for 6 hours. With a work-up procedure similar to that of Example 33, there was obtained 48.5 g of product, m.p. 172°–180° C.

(b) 3-(4-Pyridinylamino)benzamide was prepared from 3-(4-pyridinylamino)benzoic acid and ammonia according to the procedure of Example 48, part (b), and was obtained in 50% yield as a colorless powder, m.p. 201°–203° C. when recrystallized from methanol.

EXAMPLE 51

1-[3-(4-Pyridinylamino)benzoyl]piperidine was prepared from 3-(4-pyridinylamino)benzoic acid and piperidine according to a procedure analogous to that of Example 48(b), and was obtained in the form of its hydrochloride salt, colorless powder, m.p. 224°-226° C. when recrystallized from ethanol.

Evaluation of the compounds of the invention in laboratory animals has demonstrated that they possess antihypertensive activity. The primary screening test used involved oral administration to spontaneously hypertensive rats. The spontaneously hypertensive rat (SHR) is a genetically hypertensive strain developed from Wistar rats by Okamoto et al. [Jap. Circ. J. 27: 282-293 (1963)] by selective inbreeding. Unlike any other hypertensive animal model the SHR does not require any surgical intervention or chemical treatment, and it is widely recognized as a close model to essential hypertension in humans [Folkow et al., Circ. Res. 32—Hypert. Suppl. XXI, I-2: I-16 (1973); Pfeffer et al., ibid., I-28: I-38 (1973)]. The methodology used was as follows:

Male spontaneous hypertensive rats (SHR; Taconic Farms) weighing 300-350 g and with a systolic blood pressure of 160-220 mmHg were used. The rats were fasted for 18 hours prior to test agent administration. Each dose of each compound was tested in five SHR's whose blood pressure had been determined earlier that day. Systolic blood pressure measurements at various times (usually 1, 3, 5 and 24 hours) after test agent administration were obtained with a photoelectric tensometer by the ankle rubber cuff method of Kersten et al., J. Lab. Clin. Med. 32: 1090-1098 (1947). Test agents were either solubilized or suspended in 1% gum tragacanth. The starting dose usually was 30 mg (base/acid)/kg administered orally in a volume of 1 ml/kg. Further testing was done at 10, 3, 1, 0.3, etc. mg(base/acid)/kg in sequence. Testing is terminated when a dose is determined which does not cause an average reduction of ≧10 mmHg. Vehicle treated (negative control), and known standard treated (positive control) animals were tested intermittently to monitor the stability and sensitivity of the assay.

The effectiveness of a compound as an antihypertensive agent in the SHR is calculated in terms of the single oral dose (mg/kg) which lowers systolic blood pressure by 40 mmHg at any time interval tested ($AHD_{40}$).

A further test procedure employed to evaluate the activity of the compounds of the invention entailed oral administration to conscious renal hypertensive dogs. The methodology used was as follows:

Young adult mongrel dogs of either sex weighing 9-18 kg were rendered hypertensive by bilateral renal encapsulation as described by Page, J.A.M.A. 113: 2046-2048 (1939). Arterial blood pressure and heart rate were monitored daily with a sphygmomanometer for 1-2 weeks prior to medication. The dogs were then dosed orally with the test compound for 3-5 consecutive days. Blood pressure was measured at 0, 2, 4, 6 and 24 hours after dosing and for 1-2 weeks after cessation of therapy.

In several instances, the compounds of the invention were tested in the renal hypertensive dog in combination with hydrochlorothiazide, a well-known diuretic and antihypertensive agent. The combination tended to produce a more uniform antihypertensive response, and in some cases the activity of the hydrochlorothiazide was potentiated even though the compound being tested showed no significant antihypertensive activity when administered alone.

The following table gives the results of the testing on the compounds of the invention.

| Example No. | Rat $AHD_{40}$ (mg/kg) | Dog No. animals | Dog dose (mg/kg) | Dog Max change in BP (systolic/diastolic) |
|---|---|---|---|---|
| 1(b) | 5 | 6 | 0.5 | −34/−26 |
|  |  | 6 | 2 | −30/−31 |
|  |  | 3 | 10 | −20/−13 |
|  |  | 3 | 20 | −15/−22 |
| 3 | 5 | 2 | 30 | inactive |
| 4 | 6 | 2 | 20 | inactive |
| 5 | 2.5 | 3 | 10 | inactive |
| 6 | 0.5 | 2 | 20 | −32/−28 |
| 7 | 1 |  |  |  |
| 8 | 0.5 | 3 | 10 | inactive |
|  |  | 3 | 30 | inactive |
| 9 | 1.5 | 5 | 10 | (moderate decrease in 2 of 5 dogs) |
| 10 | 12 | 3 | 2.5 | −22/−17 |
|  |  | 4 | 10 | −29/−23 |
| 11 | 2.5 | 3 | 2.0 | inactive |
|  |  | 3 | 10 | inactive |
| 12 | 10 | 3 | 10 | −18/−22 (⅔ dogs) |
| 13 | 0.5 | 2 | 10 | (pressor) |
| 14 | 1.8 | 2 | 2 | inactive |
|  |  | 1 | 10 | −17/−10 |
| 15 | 8 | 2 | 2 | inactive |
|  |  | 1 | 10 | inactive |
| 16 | 10 | 3 | 10 | (pressor) |
| 17 | 40 | 2 | 10 | inactive |
| 18 | 40 | 2 | 10 | (pressor) |
| 19 | 0.6 | 3 | 10 | inactive |
| 20 | 1 | 3 | 10 | inactive |
| 21 | 0.2 | 3 | 10 | inactive |
| 22 | 10 | 2 | 10 | inactive |
| 23 | 50 | 3 | 10 | inactive |
| 24 | 10 | 2 | 10 | (pressor) |
| 25 | 20 | 2 | 10 | inactive |
| 26 | 6 | 2 | 10 | inactive |
| 27 | 20 |  |  |  |
| 28 | 25 |  |  |  |
| 29(b) | 5 | 2 | 10 | inactive |
| 30(b) | 25 | 2 | 10 | inactive |
| 31 | 10 | 2 | 10 | −20/−15 |
| 32 | 8 | 2 | 10 | −15/−15 |
|  |  | 2 | 20 | inactive |
| 33 | 2.4 | 2 | 40 | (pressor) |
| 34 | 1.4 |  |  |  |
| 35 | (−16)[a] |  |  |  |
| 36 | (−37)[a] |  |  |  |
| 37 | <1 |  |  |  |
| 38 | (−37)[a] |  |  |  |
| 39 | 19(48)[b] | 4 | 5 | −30/−22 |
| 40 | 18(15)[b] | 4 | 10 | inactive |
| 41 | 20 |  |  |  |
| 43 | >30 | 1 | 10 | −10/−10 |
| 44(b) | 2.8 |  |  |  |
| 45 | 10 |  |  |  |
| 46 | 16 |  |  |  |
| 47 | (−20)[a] |  |  |  |
| 48(b) | 2.5 | 2 | 2 | −10/−10 (1 dog) |
|  |  | 2 | 10 | −35/−22 (tolerance) |
|  |  | 2 | 20 | inactive |
| 49 | 2.5 | 2 | 10 | (pressor) |
| 50(b) | 8 |  |  |  |
| 51 | 1.8 | 3 | 10 | inactive |

[a] blood pressure drop (mmHg) at 30 mg/kg
[b] In fed rats

Many of the compounds of the invention were antihypertensively active in the rat but not in the dog. However, this is not indicative of inutility because there are several instances of clinically effective antihypertensive agents which are active in humans and in rats but not in dogs.

The compound of Example 3 was active in the renal hypertensive dog when combined with hydrochlorothiazide (10 mg/kg of each): 20-55 mm fall in blood pressure.

The compound of Example 32 was active in the renal hypertensive dog when combined with hydrochlorothiazide (10 mg/kg of each): 20-44 mm fall in blood pressure. The compound of Example 32 at a dose of 5.0 mg/kg administered intravenously lowered blood pressure by 40 mm.

The compound of Example 1(b), 1-[2-(4-pyridinylamino)benzoyl]piperidine, is an especially preferred compound. This compound caused statistically significant dose-related decreases in systolic and diastolic blood pressure of anesthetized normotensive dogs from 0.3 to 10 mg/kg, administered intravenously. It also caused a significant hypotensive effect and some reduction in heart rate in anesthetized cats when infused at dosages of 0.1, 0.3 and 1.0 mg/kg/minute.

The methiodide quaternary salt of 1-[2-(4-pyridinylamino)benzoyl]piperidine when tested in the SHR caused a 23 mmHg reduction in blood pressure at 30 mg/kg.

The effects of 1-[2-(4-pyridinylamino)benzoyl]piperidine (2 mg/kg) in combination with hydrochlorothiazide (10 mg/kg), administered orally to renal hypertensive dogs, were compared with the effects of either agent administered alone. The combination caused maximal reductions in systolic and diastolic blood pressure of 37 mmHg on the fourth day of treatment, with no effect on heart rate. The activity persisted for three days after withdrawal of treatment. The dogs appeared to respond more uniformly to the combination than to either agent alone. The peak effect of hydrochlorothiazide on diastolic blood pressure was significantly less than that achieved by the combination.

The compounds of the invention can be prepared for use by conventional pharmaceutical procedures: that is, by dissolving or suspending them in a pharmaceutically acceptable vehicle, e.g., water, aqueous alcohol, glycol, oil solution or oil-water emulsion, for parenteral or oral administration; or by incorporating them in unit dosage form as capsules or tablets for oral administration either alone or in combination with conventional adjuvants or excipients, e.g., calcium carbonate, starch, lactose, talc, magnesium stearate, gum acacia, and the like.

I claim:

1. A compound having the formula

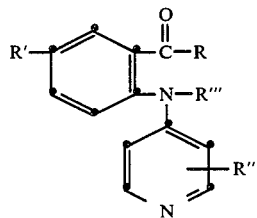

wherein R is NH₂, NH-alkyl having 1-7 carbon atoms, N(alkyl)₂ having 2-5 carbon atoms, 1-morpholinyl, 4-methyl-1-piperazinyl, or

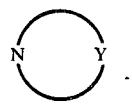

wherein
Y is a straight or branched chain alkylene radical having 4-8 carbon atoms and forming with the nitrogen atom a 5-8 membered ring, optionally substituted by a hydroxy group;
R' is H, O₂N, halogen, alkyl of 1-3 carbon atoms, alkoxy of 1-3 carbon atoms, HO or Z=NO₂S, where Z=N is amino, phenylamino, benzylamino, 4-methylbenzylamino, alkylamino or dialkylamino, alkyl having 1-3 carbon atoms;
R" is H or alkyl of 1-3 carbon atoms; and
R'" is H, 2-propenyl or alkyl of 1-3 carbon atoms; or a pharmaceutically acceptable acid-addition or quaternary ammonium salt thereof.

2. A compound according to claim 1 wherein R is

3. 1-[2-(4-Pyridinylamino)benzoyl]piperidine, according to claim 2.
4. Hexahydro-1-[2-(4-pyridinylamino)benzoyl]azepine, according to claim 2.
5. Octahydro-1-[2-(4-pyridinylamino)benzoyl]azocine, according to claim 2.
6. 1-[5-Nitro-2-(4-pyridinylamino)benzoyl]piperidine, according to claim 2.
7. 2-Methyl-1-[2-(4-pyridinylamino)benzoyl]piperidine, according to claim 2.
8. 1-[5-Hydroxy-2-(4-pyridinylamino)benzoyl]piperidine, according to claim 2.
9. 1-[5-(Benzylaminosulfonyl)-2-(4-pyridinylamino)benzoyl]piperidine, according to claim 2.
10. A compound according to claim 1 wherein R is NH-alkyl and R', R" and R'" are H.
11. N-Ethyl-2-(4-Pyridinylamino)benzamide, according to claim 10.
12. N-(n-Hexyl)-2-(4-pyridinylamino)benzamide, according to claim 10.
13. N-Isopropyl-2-(4-pyridinylamino)benzamide, according to claim 10.
14. A compound according to claim 1 wherein R is NH₂, and R', R" and R'" are H.
15. 2-(4-Pyridinylamino)benzamide, according to claim 14.
16. 5-Bromo-2-(4-pyridinylamino)benzamide, according to claim 1.
17. 4-(4-Pyridinylamino)benzamide.
18. 1-[4-(4-Pyridinylamino)benzoyl]piperidine.
19. 3-(4-Pyridinylamino)benzamide.
20. 1-[3-(4-Pyridinylamino)benzoyl]piperidine.
21. A composition for lowering the blood pressure of a hypertensive mammal which comprises an antihypertensively effective amount of a compound according to claim 1 together with one or more pharmaceutically acceptable excipients.
22. A composition according to claim 21 wherein the compound is 1-[2-(4-pyridinylamino)benzoyl]piperidine or a pharmaceutically acceptable acid-addition salt thereof.
23. A process for lowering the blood pressure of a hypertensive mammal which comprises administering to said mammal a composition according to claim 21.
24. A process for lowering the blood pressure of a hypertensive mammal which comprises administering to said mammal a composition according to claim 22.

* * * * *

UNITED STATES PATENT AND TRADEMARK OFFICE
CERTIFICATE OF CORRECTION

PATENT NO. : 4,610,991
DATED : September 9, 1986
INVENTOR(S) : Denis M. Bailey

It is certified that error appears in the above-identified patent and that said Letters Patent is hereby corrected as shown below:

Column 4, lines 13-14, "chlorosulfuric" should read -- chlorosulfonic --.

Column 5, line 15, "quanternary" should read -- quaternary --.

Column 7, line 28, "-[2-pyridinylamino)" should read -- - [2-(4-pyridinylamino)--.

Column 16, line 40, Claim 11, "-Pyridinylamino)" should read -- -pyridinylamino) --.

Signed and Sealed this

Ninth Day of December, 1986

Attest:

DONALD J. QUIGG

Attesting Officer      Commissioner of Patents and Trademarks